United States Patent
Mechoulam et al.

(10) Patent No.: US 6,531,636 B1
(45) Date of Patent: Mar. 11, 2003

(54) SYNTHETIC ENDOGENOUS CANNABINOIDS ANALOGUES AND USES THEREOF

(75) Inventors: Raphael Mechoulam, Jerusalem (IL); Esther Fride, Efrat (IL); Shimon Ben Shabat, Jerusalem (IL); Tzviel Sheskin, Jerusalem (IL); Aviva Breuer, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 3 days.

(21) Appl. No.: 09/678,120

(22) Filed: Oct. 3, 2000

Related U.S. Application Data

(63) Continuation-in-part of application No. PCT/IL99/00187, filed on Mar. 30, 1999.
(60) Provisional application No. 60/080,679, filed on Apr. 3, 1998.

(51) Int. Cl.$^7$ ........................... C07C 41/09; C07C 43/11
(52) U.S. Cl. ...................... 568/618; 514/723; 424/1.65; 568/616
(58) Field of Search ......................... 568/616; 514/723; 424/1.65

(56) References Cited

FOREIGN PATENT DOCUMENTS

WO    9412466    6/1994

OTHER PUBLICATIONS

Gideon Halperin, The Sythesis of Polyunsaturated . . . Triated at C–2, Journal of Labelled Compounds and Radiopharmaceuticals, vol. XX, No. 2, Feb. 1983, pp269–275.*
Richard B. Silverman, The Organic Chemistry of Drug Design and Drug Action, 1992, pp. 15–22.*
Mechoulam et al., Identification of . . . Cannabinoid Receptors, Biochemical Pharmacology, vol. 50, No. 1, Jun. 1995, pp. 83–90.*
J.G. Turcotte: "Synthesis of Lysophosphatidylethanolamine Analogs that Inhibit Renin Activity" Journal of Medicinal Chemistry, vol. 18, No. 12, Dec. 1975, pp. 1184–1190, XP002109045, Washington, US, p. 1189, col. 1, Table I.
F.R. Pfeiffer; "Lysophosphatidylethanolamine and 2–desoxylysophosphatidylethanolamine Derivatives. 1. Potential Renin Inhibitors" Journal of Medicinal Chemistry, vol. 14, No. 6, Jun. 1971, pp. 493–499, XP002109046, Washington, US; Tables V and VI, Compounds 12c and 13c.
J.R. Surles: "Facile Synthesis of Platelet–Activating Factor and Racemic Analogues Containing Unsaturation in the sn–1–alkyl chain" Journal of Medicinal Chemistry, vol. 28, No. 1, Jan. 1985, pp. 73–78, XP002109047, Washington, US, Scheme I; Tables I and II.

A. Wissner: "Analogues of Platelet Activating Factor. 6. Mono– and bis–aryl Phosphate Antagonists of Platelet Activating Factor" Journal of Medicinal Chemistry, vol. 35, No. 9, May 1 1992, pp. 1650–1662, XP002109048, Washington, US, p. 1651, Scheme II, R=d.

P. Sperling: "In vivo Desaturation of cis–delta–9–monounsaturated to cis–delta–9, 12–diunsaturated alkenylether glycerolipids" Journal of Biological Chemistry, vol. 268, No. 36, Dec. 25, 1993, pp. 26935–26940, XP002109049, American Society of Biological Chemists, Baltimore, MD., US, ISSN: 0021–9258, p. 26935, Abstract; Fig. 2.

W.J. Baumann: "Reactions of Aliphatic Methanesulfonates. I. Syntheses of Long–Chain Glyceryl–(1) ethers", Journal of Organic Chemistry, vol. 29, No. 10, Oct. 1964, pp. 3055–3057, XP002109050, Easton, US, Table II, Compounds XXI and XXII, p. 3057, col. 2.

R. Mechoulam: "Identification of an Endogenous 2–monoglyceride, present in Canine Gut, that Binds to Cannabinoid Receptors" Biochemical Pharmacology, vol. 50, No. 1, 1995, pp. 83–90, XP002109088, cited in the application, p. 83–p. 84.

Devane et al. Science 258: 1946–1949 (1992a).

Wagner et al, Nature 390: 518–521 (1997).

Varga et al. Eur. J. Pharmacol. 278: 279–283 (1995).

Feigenbaum et al. Eur. J. Pharmacol. 169: 159–165 (1989).

Mechoulam et al. The Therapeutic Potential of Marihuana, eds. S. Cohen, R.C. Stillman, Plenum Press, NY; pp 35–48.

Avidor et al.; J. Biol. Chem. 271: 21309–21315 (1996).

Rhee et al.; J. Med. Chem. 40: 3228–3233 (1997).

* cited by examiner

*Primary Examiner*—Rosalynd Keys
(74) *Attorney, Agent, or Firm*—Baker Botts L.L.P.

(57) ABSTRACT

The present invention relates to a compound of the general formula (I) which is a non-hydrolysable analogue of endogenous cannabinoids, which are found to be more potent therapeutic agents as they are more stable, for example, to hydrolytic cleavage in the gastrointestinal tract. The cannabinoid analogues of the invention have a therapeutic value. Therefore, pharmaceutical compositions comprising as active ingredient a therapeutically effective amount of at least one compound of the invention may be prepared. Such compositions may be used as anti-inflammatory, anti-asthmatic, analgetic, hypotensive, antiemetic or antispasmodic compositions, and as compositions for treating and/or preventing glaucoma or migraine, or as compositions for relieving symptoms of multiple sclerosis and mood stimulating compositions.

20 Claims, 4 Drawing Sheets

SYNTHETIC ENDOGENOUS CANNABINOIDS ANALOGUES AND USES THEREOF

This is a continuation-in-part of copending application Ser. No. PCT/IL99/00187 filed Mar. 30, 1999 and claims priority of U.S. patent application No. 60/080,679, filed Apr. 3, 1998 both of which are incorporated by reference herein.

STATEMENT OF THE INVENTION

The present invention relates to compounds of the general formula (I), to a process for their preparation, to pharmaceutical compositions containing at least one compound of the invention and to the different uses of said compounds.

BACKGROUND OF THE INVENTION

Anandamide and 2-arachidonoyl glycerol (2-Ara-Gl) represent the two types of endogenous cannabinoid constituents discovered so far [Devane W. A. et al., Science 258:1946–1949 (1992a); Mechoulam R. et al., Biochem. Pharmacol 50:83–90 (1995); Mechoulam R. et al., U.S. Pat. No. 5,618,858 (corresponding to IL 103932)]. These compounds and related amides and esters thereof cause numerous effects which have therapeutic potential [Mechoulam R. et al., Progress in Medicinal Chemistry 35:501–545, GP Ellis Ed. (1998); Mechoulam R. (ed.,), Cannabinoids as therapeutic agents CRC Press Coca Ratio Florida (1986)]. It has been recently shown that anandamide may be an endogenous modulator of blood pressure [Wagner J. A. et al., Nature 390:518–521 (1997)]. When administered to rats it was shown to reduce blood pressure [Varga K. et al., Eur. J. Pharmacol 278:279–283 (1995)]. These findings were confirmed by the inventors [see Table 3]. However, both anandamide and 2-arachidonoyl glycerol are prone to easy and rapid enzymatic hydrolysis. This represents a serious drawback in their eventual use as drugs, inter alia, because substances which are susceptible to hydrolytic cleavage may undergo changes in the gastrointestinal tract.

The inventors have discovered a novel group of related synthetic derivatives of 2-archidonoyl glycerol which are stable to hydrolysis. These are ethers derived from long chain fatty alcohols (in particular archidonyl alcohol). These compounds bind to the $CB_1$ and $CB_2$ cannabinoid receptors and exhibit in vivo effects similar to those of anandamide and 2-Ara-Gl. The compounds disclosed herein reduced intraocular pressure in rabbits (a model for glaucoma), reduce pain and vomiting, lower blood pressure, exhibit anti-inflammatory properties, have anti-spasticity effects and may thus be useful in the treatment of multiple sclerosis. Moreover, the effect of the novel compounds is prolonged, which for some diseases is a distinct advantage.

SUMMARY OF THE INVENTION

The present invention relates to a compound of the general formula (I):

$$R^1\text{—}CH_2\text{—}O\text{—}CHR^2R^3 \qquad (I)$$

wherein $R^1$—$CH_2$— represents an alkenyl moiety derived form a polyunsaturated fatty alcohol of form 18 to 28 carbon atoms containing 3 to 6 double bonds, wherein the first double bond is positioned at C-3, C-6 or C-9 when counting from the free end of said alkenyl moiety; $R^2$ represents a hydrogen atom or a lower $C_1$–$C_5$ alkyl group; and $R^3$ represents a 2-glyceryl group, or an alkoxyalkyl group, wherein the $R^3$ alkoxyalkyl group includes a branched or straight chain alkyl moiety; said $C_1$–$C_5$ alkyl and alkoxyalkyl groups may be, independently, substituted by one or more hydroxyl groups, amino groups or alkylamino groups on any one of the carbon atoms therein, said hydroxyl group may be further substituted to form an ester or be converted into a phosphonate or alkyl sulphonate group.

Further, the invention relates to a process for preparing the compounds of the invention, which process comprises the steps of (a) reacting a compound of general formula (II):

$$R^1\text{—}CH_2\text{—}OH \qquad (II)$$

wherein $R^1$ is as defined above for compounds of general formula (I), with an alkylsulfonyl halide or arylsulphonyl halide; (b) reacting the product obtained in step (a) with either (i) an alcohol of the general formula (III):

$$R^2R^3CHOH \qquad (III)$$

wherein $R^2$ and $R^3$ are as defined above for compounds of general formula (I), in the presence of a base; or with (ii) a alkylidene or arylidene glycerol having one free hydroxyl group at the 2-position, in the presence of a base; and optionally (c) when said product of step (a) is reacted in step (b) with alkylidene or arylidene glycerol, the product of said step (b) is further reacted with an acidic reagent to obtain the compound of general formula (I):

Yet further, the invention relates to a pharmaceutical composition comprising as active ingredient an therapeutically effective amount of at least one compound of the invention and optionally further comprising pharmaceutically acceptable carriers, adjuvants, diluents and additives.

DETAILED DESCRIPTION OF THE INVENTION

Cannabinoids are organic substances present in *Cannabis sativa*, having a variety of pharmacological properties. Endogenous cannabinoids are fatty acid derivatives present in mammals, which have pharmacological properties similar to those of the plant cannabinoids. The present invention relates to non-hydrolysable derivatives of endogenous cannabinoids.

In particular, the invention relates to a compound of the general formula (I):

$$R^1—CH_2—O—CHR^2R^3 \quad (I)$$

wherein the moiety $R^1$—$CH_2$— represents an alkenyl moiety derived from a polyunsaturated fatty alcohol of form 18 to 28 carbon atoms, the alkenyl moiety containing 3 to 6 double bonds, wherein the first double bond is positioned at C-3, C-6 or C-9, when counting from the free end of said alkenyl moiety; $R^2$ represents a hydrogen atom or a lower $C_1$–$C_5$ alkyl group; and $R^3$ represents a 2-glyceryl group, or an alkoxyalkyl group, wherein the $R^3$ alkoxyalkyl group includes a branched or straight chain alkyl moiety; wherein said $C_1$–$C_5$ alkyl and said alkoxyalkyl groups may be, independently, substituted by one or more hydroxyl groups, amino groups or alkylamino groups on any one of the carbon atoms therein, said hydroxyl group may be further substituted to form an ester or be converted into a phosphonate or alkyl sulphate group.

Preferably, the alkenyl moiety within the compound of the invention is selected from the group consisting of octadecatrienyl, eicosapentaenyl, docosahexaenyl, eicosatrienyl or eicosatetraenyl.

Figure 5:
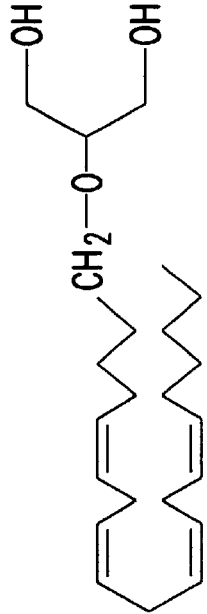
FIG. 5 illustrates the structure of some compounds of formula I.
Figure 5:
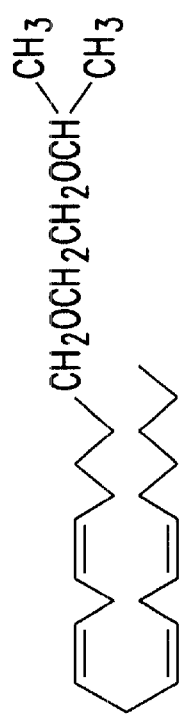
Figure 5:
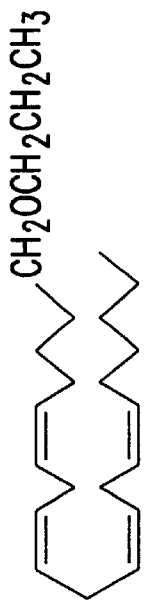

As disclosed in the following Examples, the specific embodiments of the invention, are 2-dihomo-γ-linolenyl glyceryl ether and arachidonyl-2-isopropoxyethyl ether and particularly, 2-arachidonyl glyceryl ether (FIG. 5). These compounds are shown to have a therapeutic value as they are capable of binding for a prolonged period of time to the $CB_1$ and $CB_2$ cannabinoid receptors.

The compounds of the invention may be radiolabeled and employed in numerous biological, clinical and diagnostic procedures. As the derivatives of the invention have the chemical nature of an ether, they are more stable than the endogenous cannabinoid 2-arachidonoyl glycerol and therefore may allow observation of their pharmaceological profile over a longer period of time compared to the corresponding endogenous compounds.

Figure 1:
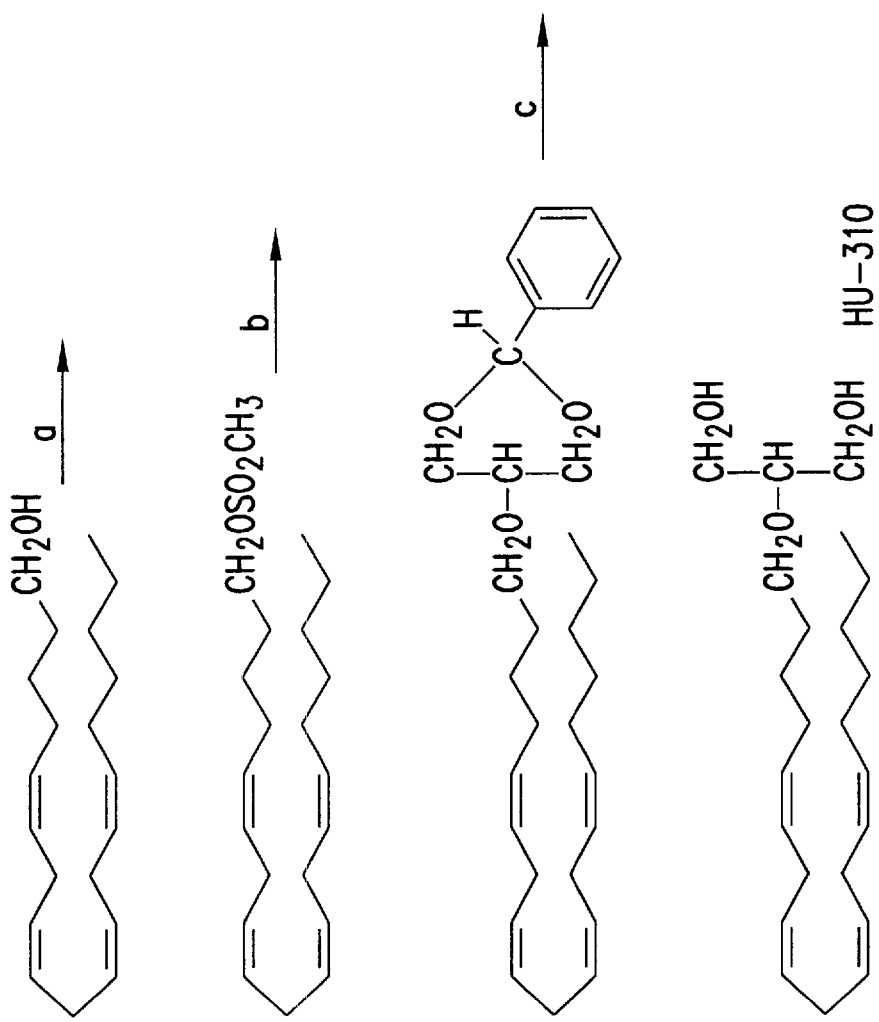
FIG. 1 shows a schematic illustration of the process for preparing 2-O-arachidonyl glycerol, employing the following reagents and conditions: (a) Methanesulfonyl chloride, pyridine, room temperature (RT), 5 hours (hrs); (b) cis-1,3-benzylideneglycerol, KOH, 3 hrs; (c) HCl:methanol (3:7) 20 hrs.
Figure 2:
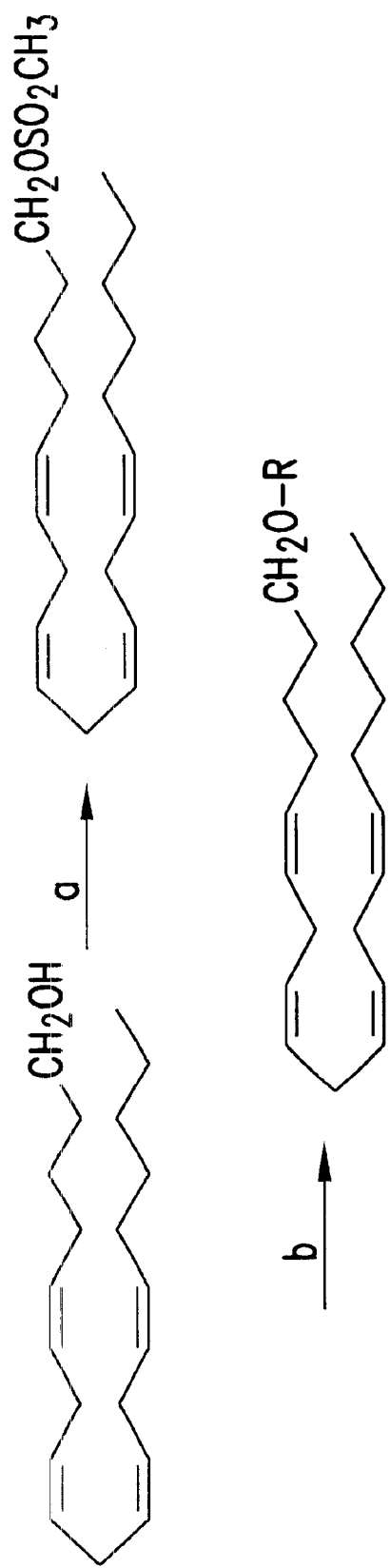
FIG. 2 shows a schematic illustration of a second route of performing the process of the invention, in which 2-O-arachidonyl ethers may be obtained, in which the following reagents and conditions are employed: (a) Methanesulfonyl chloride, pyridine, RT, 5 hrs; (b) R-OH, KOH, 3 hrs., wherein R represents the group —$CHR^2R^3$ as herein defined.

In a second aspect, the invention relates to a process for the preparation of a compound of general formula (I):

$$R^1—CH_2—O—CHR^2R^3 \quad (I)$$

wherein $R^1$—$CH_2$— represents an alkenyl moiety derived from a polyunsaturated fatty alcohol of form 18 to 28 carbon atoms with 3 to 6 double bonds with the first double bond at the C-3, C-6 or C-9 position counting from the free end of said alkenyl moiety; $R^2$ represents a hydrogen atom or a lower $C_1$–$C_5$ alkyl group; and $R^3$ represents a 2-glyceryl group, or an alkoxyalkyl group, wherein the $R^3$ alkoxyalkyl group includes a branched or straight chain alkyl moiety; wherein said $C_1$–$C_5$ alkyl and alkoxyalkyl groups may be, independently, substituted by one or more hydroxyl groups, amino groups or alkylamino groups, on any one of the carbon atoms, said hydroxyl group may be further substituted to form an ester or be converted to a phosphonate or to an alkyl sulphonate; which process comprises the steps of:
(a) reacting a compound of general formula (II):

$$R^1—CH_2—OH \quad (II)$$

wherein $R^1$ is as defined above, with an alkylsulfonyl halide or arylsulphonyl halide; (b) reacting the product obtained in step (a) with either (i) an alcohol of the general formula (III):

$$R^2R^3CHOH \quad (III)$$

wherein $R^2$ and $R^3$ are as defined above, in the presence of a base; or with (ii) a alkylidene or arylidene glycerol having one free hydroxyl group at the 2-position, in the presence of a base; (c) optionally, when said product of step (a) is reacted in step (b) with said alkylidene or arylidene glycerol, the product of said step (b) is further reacted with an acidic reagent to obtain the compound of general formula (I). The two modes of performing the process of the invention are illustrated in FIG. 1 and FIG. 2.

The alkylsulfonyl halide utilized in the process of the invention is preferably methanesulfonyl chloride, whereas, the arylsulfonyl halide employed is preferably para-toluene sulfonyl chloride.

In the process of the invention, the preferred alcohol employed is an isoalkoxy alcohol, and more preferably, 2-isopropoxy alcohol or propanol. The arylidene glycerol employed is preferably cis-1,3-benzylidene glycerol.

According to one embodiment of the invention, the reaction steps are carried out in the presence of KOH as the base, at room temperature, under nitrogen atmosphere. When necessary to use an acidic reagent, the preferred reagent is a mixture of HCl and methanol, preferably with a ratio of 1:7.

Evidently, any compound obtained by the method of the invention, is within the scope of the invention.

In a third aspect, the invention relates to a pharmaceutical composition comprising as active ingredient a therapeutically effective amount of at least one compound of general formula (I):

$$R^1—CH_2—O—CHR^2R^3 \quad (I)$$

wherein $R^1$—$CH_2$— represents an alkenyl moiety derived from a polyunsaturated fatty alcohol of from 18 to 28 carbon atoms containing 3 to 6 double bonds, wherein the first double bond is positioned at C-3, C-6 or C-9 when counting from the free end of said alkenyl moiety; $R^2$ represents a hydorgen atom or a lower $C_1$–$C_5$ alkyl group; and $R^3$ represents a 2-glyceryl group, or an alkoxyalkyl group, wherein the $R^3$ alkoxyalkyl group includes a branched or straight chain alkyl moiety; wherein said $C_1$–$C_5$ alkyl and alkoxyalkyl groups may be, independently, substituted by one or more hydroxyl groups, amino groups or alkylamino groups on any one of the carbon atoms therein, said hydroxyl group may be further substituted to form an ester or be converted into a phosphonate or alkyl sulphonate group, which composition may further comprise acceptable carriers, adjuvants, additives, diluents and/or preserving agents.

The pharmaceutical composition of the invention may be used for numerous therapeutic purposes, inter alia, as anti-inflammatory, anti-asthmatic, analgesic, hypotensive, anti-emetic or anti-spasmodic compositions, as compositions for treating and/or preventing glaucoma or migraine, as compositions for relieving symptoms of multiple sclerosis and mood-stimulating compositions.

According to some particular embodiments of the invention, the composition comprise as active ingredient 2-arachidonyl glyceryl either, 2-dihomo-γ-linolenyl glyceryl ether, 2-isopropoxyethyl ether, a combination of the same or a combination of the same with other therapeutically active ingredients.

The compositions of the invention may be administered and dosed in accordance with good medical practice, taking into account the clinical condition of the individual patient, the site and method of administration, scheduling of administration, patient's age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art, for example, inflammation, hypertension, glaucoma and other disorders and symptoms.

The doses may be single doses or multiple doses over a period of several days, but single doses may be preferred.

The pharmaceutical composition of the invention can be administered in various ways and may comprise, in addition to the active ingredient, pharmaceutically acceptable carriers, diluents, adjuvants, preserving agents and vehicles. The pharmaceutical compositions can be administered subcutaneously or parentally including intravenous, intraaterial, intramuscular, and intraperitoneal administration, as well as intrathecal techniques. Implants of the pharmaceutical preparations may also be useful. The pharmaceutically acceptable carriers, diluents, adjuvants and vehicles as well as implant carriers generally refer to inert, non-toxic solid or liquid fillers, diluents, or encapsulating material not reacting with the active ingredients of the invention.

When administering the pharmaceutical composition of the invention parentally, it will generally be formulated in a unit dosage injectable form (solution, suspension, emulsion). The pharmaceutical formulations suitable for injection include sterile aqueous solutions and sterile powders for reconstitution into sterile injectable solutions. The carrier can be any physiologically acceptable suitable carrier, for example, water, or aqueous buffer solutions.

In addition, various additives which enhance the stability, sterility or/and isotonicity of the compositions, including antimicrobial preservatives, antioxidants, chelating agents and buffers can be added. Prevention of the action of microorganisms can be ensured by various antibacterial and antifungal agents, for example, parabens, chlorobutanol, phenol, sorbic acid and the like. In many cases it will be desirable to include isotonic agents, for example, sugars, sodium chloride, and the like. Prolonged absorption of the pharmaceutical form and be brought about by the use of agents delaying absorption, for example, aluminum monostearate and gelatin. According to the present invention, any vehicle, diluent, or additive used would have to be compatible with the compositions.

Conventional forms such as administering the composition as tablets, suspensions, solutions, emulsions, capsules, powders, syrups and the like may also be used. Known techniques which deliver it orally or intravenously and retain the biological activity are preferred.

According to one preferred embodiment, the compositions of the invention comprise from about 1 mg to about 100 mg of the active ingredient per dosage unit form.

In yet a further aspect, the invention relates to the use of the compound of general formula (I) as herein before defined in the preparation of a pharmaceutical composition. Nonetheless, the compound of the invention may be used for diagnostic purposes as well known to the man of the art and as also briefly described herein before. Accordingly, the compound will be labeled by a suitable labeling moiety, such as $^3H$ or $^{13}C$.

The present invention is defined by the claims, the contents of which are to be read as included within the disclosure of the specification.

The invention will known be described in an illustrative manner, and it is to be understood that the terminology which has been used is intended to be used in the nature of words of description rather than of limitation. Obviously, many modifications and variations of the present invention are possible in light of the above teachings. It is, therefore, to be understood that within the scope of the appended claims, the invention may be practiced otherwise than as specifically described.

EXAMPLES

Example 1

Synthesis of 2-O-Arachidonyl glyceryl ether (HU-310) (FIG. 1)

Arachidonyl alcohol (0.34 mmol, 100 mg) in dry pyridine (5 ml) was cooled to 0° C. Methane sulfonyl chloride (0.52 mmol; 40 mg) was added to the above solution under a nitrogen atmosphere. The reaction mixture was slowly brought to room temperature at which the reaction was continued for 5 hours. Water (20 ml) and ether (20 ml) were then added to the reaction mixture after which the organic phase was separated, washed with 2N sulfuric acid, then with water and then with a 10% solution of potassium carbonate. The reaction mixture was dried by evaporation of the solvents to obtain an the oily product arachidonyl methane sulfonate, (75 mg; yield 59%) exhibiting the following: $^1H$ HMR (CDCl$_3$) δ 5.34–5.41 (m, 8H), 4.23 (t, J=6.6 Hz, 2H), 3.00 (s, 3H), 2.75–2.84 (m, 6H), 2.04–2.12 (m, 4H), 1.65–1.74 (m, 2H), 1.33–1.50 (m, 2H), 1.25–.130 (m, 6H), 0.89 (t, J=7.2 Hz, 3H). IR (cm$^{-1}$): 2900, 2850, 1350, 1170, 940.

The oily product obtained as described hereinabove (0.22 mmol; 64 mg) was added to a mixture of cis-1,3-benzylideneglycerol (0.214 mmol; 39 mg) and potassium hydroxide (170 mg) in dry benzene (10 ml) and was allowed to react at room temperature, under nitrogen atmosphere. The mixture was then washed with water, followed by with a 10% hydrochloric acid solution and then again with water. The mixture was then dried with sodium sulfate after which the solvent was evaporated and the product transferred through a column chromatography to provide the oily product, 2-O-arachidonyl-1,3-benzylideneglycerol, (26 mg, yield 33%). The product obtain exhibited the following: $^1H$ NMR (CDCl$_3$) δ 7.48–7.52 (m, 2H), 7.33–7.38 (m, 3H), 5.54 (s, 1H), 5.32–5.41 (m, 8H), 4.32 (d, J=12.6 Hz, 2H), 4.03 (d, J=14.1 Hz, 2H), 3.55 (t, J=6.6 Hz, 2H), 3.25 (m, 1H), 2.75–2.84 (m, 6H), 2.04–2.18 (m, 4H), 1.60–1.70 (m, 2H), 1.20–1.38 (m, 8H) 0.88 (t, J=6.9 Hz, 3H). IR (CM$^{-1}$): 2900, 2850, 1450, 1380, 1340, 1150, 1100.

The above obtained oil, 2-O-arachidonyl-1,3-benzylideneglycerol, was then dissolved in a mixture of methanol and concentrated hydrochloric acid (7:3, 10 ml) and allowed to react for 3 hrs. at room temperature, under nitrogen atmosphere, after which the methanol was evaporated under reduced pressure and the acid residue was removed by azeotropic distillation with benzene to provide the desired product 2-O-arachidonyl glyceryl ether (herein referred to also sa HU-310) in the form of a yellowish oil. The product, (35 mg, yield 87%) exhibited the following: (1) $^1H$ NMR (CDCl$_3$) δ 5.34–5.39 (m, 8H), 3.66–3.79 (m, 4H), 3.58 (t, J=6.6 Hz, 2H), 3.43–3.46 (m, 1H), 2.75–2.84 (m, 6H), 1.99–2.20 (m, 4H), 1.60–1.70 (m, 2H), 1.20–1.42 (m, 8H), 0.89 (t, J=6.9 Hz, 3H), IR (cm$^{-1}$); 3350, 290, 2850, 1440, 1040. (2) GC-MS (EI) after silylation with BSTFA exhibited M$^+$ at m/z 508. [M-15]$^+$ at m/z 493, while m/z obtained were 405, 383, 272, 219, 150, 129, 103 and 73.

Other ethers, such as 2-dihomo-γ-linolenyl glyceryl ether (herein also referred to as HU-314) and arachidonyl-2-isopropoxyethyl ether (herein also referred to as HU-313) were prepared by reacting the arachidonyl methane sulfonate with an alcohol, such as 2-isopropyloxy ethanol and propanol, respectively (FIG. 2). The products were obtained in good yield (60–70%).

Example 2

Biological Assays and Results

Analgesia

The novel compounds prepared as described above were evaluated for their potency in reducing analgesia, according to the standard hot plate test, as briefly described hereinafter.

The compounds of the invention (HU-310, HU-313 and HU-314) wee dissolved in a detergent (Emulphomethanol:saline (5:5:90)) mixture and administered by intravenous injection in the tail vein of mice with an injection volume of 0.1 ml/10 g of body weight. The results presented in Table 1 indicate that all three compound of the invention are potent analgetic agents, wherein HU-310 being the most potent.

TABLE 1

Analgesia reduction in mice

| Compound | Analgesia, $ED_{50}$ (mg/kg) |
|---|---|
| HU-310 | 2.8 |
| HU-313 | 3.5 |
| HU-314 | 4.6 |

Antiemetic Activity

The compounds of the invention were also evaluated for their potency as an antiemetic agent following the procedure described by Feigenbaum et al., [Eur. J. Pharmacol. 169:159–165 (1989, wherein pigeons suffering from emesia caused by an antineoplastic drug (cisplatin) were used as the model.

Accordingly, each compound was dissolved in Emulphor (detergent):ethanol:saline (5:5:90) and administered subcutaneously to the pigeons. The injection volume was 1.0 ml/kg body weight. Reduction of vomiting with 2-O-Arachidonyl glyceryl ether (HU-310) was 50% when using 3.0 mg of the active ingredient per kg body weight. In case of 2-dihomo-γ-linolenyl glyceryl ether (HU-314) and arachidonyl-2-isopropoxyethyl ether (HU-313), vomiting was also reduced, however to a lesser extent.

Antiglaucoma Activity

Each compound was further evaluated for their potency as agent for treating and/or preventing glaucoma. Accordingly, stable glaucoma was induced in rabbits by injecting into the eye δ-chymotrypsin as described by Mechoulam R. et al., [Mechoulam R. et al., The Therapeutic Potential of Marihuana eds S. Cohen, R. C. Stillman Plenum Press, N.Y., pp. 35–48 (1975)]. As a control, pilocarpine, a standard antiglaucoma drug, was employed showing intraocular pressure (I.O.P.) reduction at a concentration of 0.01% in aqueous solution and provided a period of 30 hours delay in the recovery of the original chymotrypsin-induced IOP.

The compounds of the invention were each dissolved in a detergent (Emulphor:ethanol:saline (5:5:90)) mixture and then further diluted with saline to obtain the desired concentrations. The compounds were found to be active in reducing I.O.P. When administered to the eye at a concentration of 0.1% they delayed the recovery of the original chymotrypsin-induced IOP for about 4–10 hours.

Anti-inflammatory Activity

The potency of each of the compounds of the invention were evaluated for their potency to act as anti-inflammatory agents, according to the method described Calhoun W. et al., [Calhoun W. et al. Agents and Actions 21:306–309 (1987)]. In the method, water was substituted for mercury as the displacement medium. Platelet Activating Factor (PAF) (1.0 μg) or arachidonic acid (1.0 mg) dissolved in 50 μg of a saline buffer containing 5% ethanol were injected subcutaneously into the plantar surface of the right hind paw of ether anaesthetized female mice (20–25 gr). The volume of the right foot was measured to the level of the lateral malleous by water displacement before treatment and 15 min after PAF injection or 30 min after arachidonic injection. The change in paw volume was calculated for each mouse. Table 2 presents the inhibition of archidonic acid induced paw swelling. The values obtained are measured as the increase in paw volume using a plethysmometer. The degree of swelling was expressed as the percentage in drug-treated mice compared to inhibition of paw edema from vehicle (Emulphor:ethanol:saline) treated controls (95% significance by ANOVA. N=5 mice/group). Control animals received peanut oil (50 μl). The results clearly show that both HU-310 and HU-313 are potent anti-inflammatory agents.

TABLE 2

Inhibition of Arachidonic Acid-induced Paw Edema[a,b]

| Dose (mg/kg) | HU-310 | HU-313 |
|---|---|---|
| 5 | 70.2 | 62.20 |
| 10 | 92.2 | 72.02 |
| 25 | 100.0 | 94.04 |

Hypertension

To evaluate the potency of the compounds of the present invention as anti-hypertension agents, each compound was dissolved in a mixture of ethanol:emulphor:saline (1:1:18) and administered to non-anaestisized rats, cannulated through the aorta (for injection) and the jugular view (for measurements of blood pressure). Injection of saline or of the dissolution mixture (ethanol:emulphor:saline) did not show any effect on the medium arterial pressure while HU-310 exhibited a significant effect on the arterial pressure. Table 3 presents the effect of HU-310 in comparison with anandamide (ANA) and 2-Ara-GL. The following data indicate that whereas the endogenous cannobinoid 2-ARA-GL induced a moderate, short-lasting hypotension, HU-310 induced a significantly more profound and longer-lasting decrease in blood pressure.

TABLE 3

Comparison of hypotensive effects of ANA, 2-ARA-GL and HU-310

| Drug[a] | Maximal hypotension[b] (mm Hg) | Latency to maximal effect (min.) | Time of recovery (min) |
|---|---|---|---|
| ANA | 15 | 2.0 | 7.0 |
| 2-Ara-GL | 34 | 7.2 | 13.0 |
| HU-310 | 105 | 34.0 | 75.0 |

[a]Dose: 12 mg/Kg
[b]The values provided indicate the difference between the mean arterial pressure before and after drug administration.

Binding of the compounds of the invention to the $CB_1$ and $CB_2$ cannabinoid receptors Binding to $CB_1$ Binding of the active compounds to $CB_1$ receptor was determined according to the procedure described by Devane et al. [Devane et al., J. Med. Chem. 35:2065–2069 (1992b)], as wee the preparation of the synaptosomal membrane and the ligand binding assay. According to this method, the competetive binding of the active compounds of the invention was determined employing [$^3H$]HU-243 which is the labeled form of $5^1$-(1,1-dimethylheptyl)-7-hexahydrocannabinol also described by Devane et al [Devane et al. (1992b) ibid.]

In principle, 4 $\mu$g of synaptosomal membrane protein were homogenized in 50 mM Tris-HCl, 2 mM $MgCl_2$ and 1 mM EDTA pH 7.4 to obtain the binding mixture having a final concentration of 60 pM, with which the Ki was determined according to the assay described by Devane et al. [Devane et al. (1992) ibid.]. The Ki value obtained for HU-310 according to this method was 62.3±3.0 $IC_{50}$. Ki values were calculated according to following known equation: $Ki-IC_{50}/(1+[L]/Kd)$ wherein $IC_{50}$ is the concentration of a compound that will reduce a specific binding of a given radioligand by 50%; [L] is the concentration of the radioligand used in the assay and Kd is the dissociation constant for the radioligand (see also FIG. 3).

Binding to $CB_2$

Binding to $CB_2$ receptors of African green monkey kidney cells (COS cells) was determined by first transiently transfected these cells with suitable plasmids containing a sequence encoding $CB_2$ bound to a carrier (5 $\mu$g/100 mm dish), using DEAE-dextran method [Avidor R. et al. J. Biol. Chem. 271:21309–21315 (1996)]. Two days later the cells were washed with phosphate-buffered saline (PBS), scraped, pelleted, and stored at −80° C., after which the cell's pellet was homogenized in 50 mM Tris-HCl, 5 mM $MgCl_2$, and 2.5 mM EDTA, pH 7.4. The ligand-containing mixture was further supplemented with 10 MM $CaCl_2$ to obtain the binding mixture, in which the final concentration of the radiolabeled ligand [$^3H$]HU-243 was 300 pM. Determination of Ki values were then obtained as described Rhee et al. [Rhee et al. J. Med. Chem. 40:3228–3233 (1997)]. Accordingly, the Ki value obtained for HU-310 according to this method was 459.4±118.2 (FIG. 4).

Figure 3:
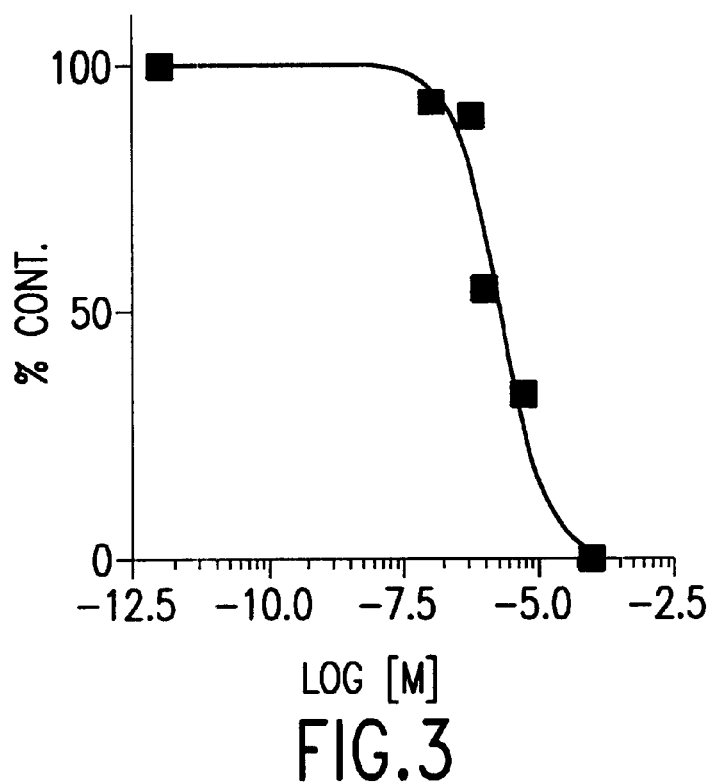
FIG. 3 illustrates the competitive inhibition of [$^3$H]HU-243 binding on the receptor $CB_1$ by HU-310 (), %Cont. Indicates the % from control.
Figure 4:
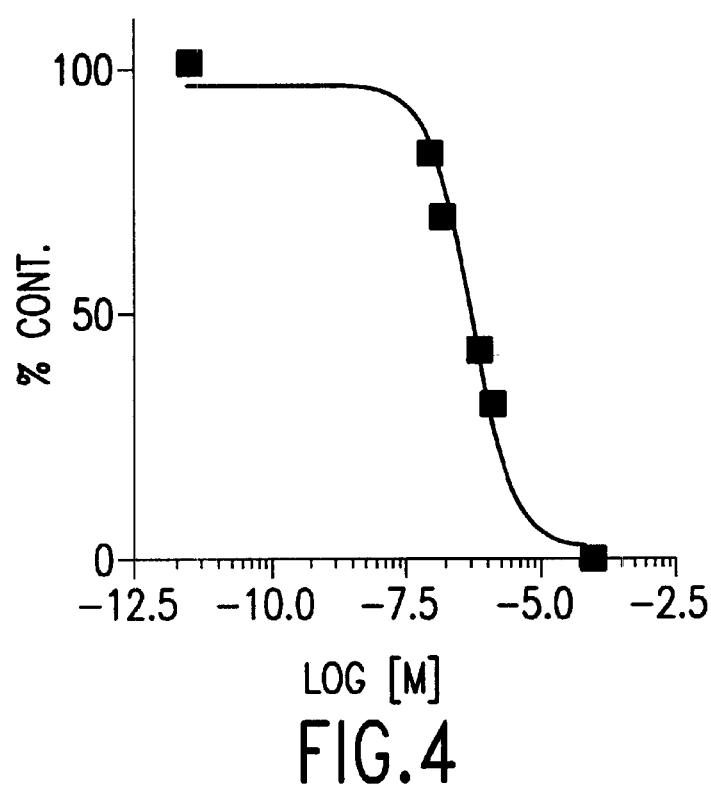
FIG. 4 illustrates the competitive inhibition of [$^3$H]HU-243 binding on the receptor $CB_2$ by HU-310 (), %Cont. indicates the % from control.

The binding of 2-arachidonyl glyceryl ether to $CB_1$ and to $CB_2$ is shown in FIG. 3 and FIG. 4, respectively. The results indicate that HU-310 is a potent substrate for the two cannabinoid receptors $CB_1$ and $CB_2$.

We claim:

1. A compound of the general formula:

wherein
$R^1$—$CH_2$ represents an alkenyl moiety derived from a polyunsaturated fatty alcohol of from 18 to 28 carbon atoms containing 3 to 6 double bonds, wherein the first double bond is positioned at C-3, C-6 or C-9 when counting from the free end of said alkenyl moiety;
$R^2$ represents a hydrogen atom or a lower $C_1$–$C_5$ alkyl group; and
$R^3$ represents an alkoxyalkyl group;
or the group $CHR^2R^3$ represents a 2-glyceryl group;
$C_1$–$C_5$ alkyl and alkoxyalkyl groups may be, independently, substituted by one or more hydroxyl groups, amino groups or alkylamino groups on any one of the carbon atoms therein, which each hydroxyl group may be further substituted to form an ester or may be converted into a phosphonate group.

2. The compound according to claim 1, wherein said alkenyl moiety is selected from the group consisting of octadecatrienyl, eicosapentaenyl, docosahexaenyl, eicosatrienyl and eicosatetranyl.

3. The compound according to claim 2, selected from the group consisting of 2-arachidonyl glyceryl ether, 2-dihomo-γ-linolenyl glyceryl ether and arachidonyl-2-isopropoxyethyl ether.

4. A radiolabeled compound according to claim 1.

5. A process for the preparation of a compound of general formula (I):

wherein
$R^1$—$CH_2$ represents an alkenyl moiety derived from a polyunsaturated fatty alcohol of from 18 to 28 carbon atoms with 3 to 6 double bonds with the first double bond at the C-3, C-6 or C-9 position counting from the free end of said alkenyl moiety;
$R^2$ represents a hydrogen atom or a lower $C_1$–$C_5$ alkyl group; and
$R^3$ represents an alkoxyalkyl group;
or the group $CHR^2R^3$ represents a 2-glycerol group;
said $C_1$–$C_5$ alkyl group and alkoxyalkyl groups may be, independently, substituted by one or more hydroxyl groups, amino groups or alkylamino groups, on any one of the carbon atoms, each hydroxyl group may be further substituted to form an ester or may converted to a phosphonate or to an alkyl sulphonate,
which process comprises the steps of:
a) reacting a compound of general formula (II):

wherein $R^1$ is as defined above, with an alkylsulfonyl halide or arylsulphonyl halide;
(b) reacting the product obtained in step (a) with either (i) an alcohol of the general formula (III):

wherein $R^2$ and $R^3$ are as defined herein above, in the presence of a base;
or with (ii) a alkylidene or arylidene glycerol having one free hydroxyl group at the 2-position, in the presence of a base;
optionally, when said product of step (a) is reacted in step (b) with said alkylidene or arylidene glycerol, the product of said step (b) is further reacted with an acidic reagent to obtain the compound of general formula (I).

6. The process according to claim 5, wherein said alkylsulfonyl halide is methanesulfonyl chloride and said arylsulfonyl halide is paratoluene sulfonyl chloride.

7. The process according to claim 5, wherein said alcohol is an isoalkoxy alcohol.

8. The process according to claim 5, wherein said reaction is carried out in the presence of KOH.

9. The process according to claim 5, wherein arylidene glycerol is cis-1,3,-benzylidene glycerol.

10. The process according to claim 5, wherein said acidic reagent is a mixture of HCl and methanol.

11. The process as claimed in claim 5, wherein said reaction steps are carried out at room temperature, under nitrogen atmosphere.

12. A pharmaceutical composition comprising as active ingredient a therapeutically effective amount of at least one compound of general formula (I):

$$R^1\text{—}CH_2\text{—}O\text{—}CHR^2R^3 \qquad (I)$$

wherein
- $R^1\text{—}CH_2$ represents an alkenyl moiety of a polyunsaturated fatty alcohol of from 18 to 28 carbon atoms containing 3 to 6 double bonds, wherein the first double bond is positioned at C-3, C-6 or C-9 when counting from the free end of said alkenyl moiety;
- $R^2$ represents a hydrogen atom or a lower $C_1$–$C_5$ alkyl group; and
- $R^3$ represents an alkoxyalkyl group;
- or the group $CHR^2R^3$ represents a 2-glyceryl group;

said $C_1$–$C_5$ alkyl and alkoxyalkyl groups may be, independently, substituted by one or more hydroxyl groups, amino groups or alkylamino groups on any one of the carbon atoms therein, which each hydroxyl group may be further substituted to form an ester or may be converted into a phosphonate or alkyl sulphonate group, which composition may further comprise acceptable carriers, adjuvants, additives, diluents and/or preserving agents.

13. The composition according to claim 12 wherein said active ingredient is selected from 2-arachidonyl glyceryl ether, 2-dihomo-γ-linolenyl glyceryl ether and arachidonyl-2-isopropoxyethyl ether.

14. The composition according to any one of claims 12 to 13 in a dosage unit form.

15. The composition according to claim 14 comprising from about 1 mg to about 100 mg of the active ingredient per dosage unit form.

16. A composition according to claim 1 wherein the $R^3$ alkoxyalkyl group includes a branched or straight chain alkyl moiety.

17. A pharmaceutical composition according to claim 12 wherein the $R^3$ alkoxyalkyl group includes a branched or straight chain alkyl moiety.

18. The process of claim 5 wherein the $R^3$ alkoxyalkyl group includes a branched or straight chain alkyl moiety.

19. The process of claim 10 wherein the ratio of HCl to methanol is 1:7.

20. The process according to claim 5 wherein said alcohol is an isoalkyoxy alcohol.

* * * * *